US011433228B2

(12) United States Patent
Grant et al.

(10) Patent No.: US 11,433,228 B2
(45) Date of Patent: Sep. 6, 2022

(54) SINGLE USE CAPS AND COVERS FOR VASCULAR ACCESS DEVICES, AND KITS AND METHODS FOR USING THE SAME

(71) Applicant: CleanSite Medical, Inc., Solana Beach, CA (US)

(72) Inventors: John Grant, Solana Beach, CA (US); Daniel M. Chambers, Solana Beach, CA (US)

(73) Assignee: CleanSite Medical, Inc., Solana Beach, CA (US)

( * ) Notice: Subject to any disclaimer, the term of this patent is extended or adjusted under 35 U.S.C. 154(b) by 0 days.

(21) Appl. No.: 17/180,661

(22) Filed: Feb. 19, 2021

(65) Prior Publication Data

US 2021/0170157 A1    Jun. 10, 2021

Related U.S. Application Data

(63) Continuation of application No. 17/115,626, filed on Dec. 8, 2020, which is a continuation of application No. PCT/US2020/060310, filed on Nov. 12, 2020.
(Continued)

(51) Int. Cl.
*A61M 39/20* (2006.01)
*A61M 39/02* (2006.01)
(Continued)

(52) U.S. Cl.
CPC ............. *A61M 39/20* (2013.01); *A61M 5/50* (2013.01); *A61M 39/0208* (2013.01);
(Continued)

(58) Field of Classification Search
CPC ............ A61M 39/20; A61M 2039/205; A61M 2205/0205; A61M 2205/273; A61M 5/50;
(Continued)

(56) References Cited

U.S. PATENT DOCUMENTS 4,286,640 A   9/1981  Knox et al.
5,104,379 A   4/1992  Nakamura et al.
(Continued)

OTHER PUBLICATIONS

International Search Report, PCT/US20/60310, dated Feb. 25, 2021, 2 pages.

*Primary Examiner* — Shefali D Patel
(74) *Attorney, Agent, or Firm* — Acuity Law Group, P.C.; Daniel M. Chambers

(57) ABSTRACT

This invention concerns improved single use caps or covers for vascular access devices such as needlefree connectors that are used, for example, in intravenous administration sets and extension sets. Removal of a single use cap or cover according to the invention from a vascular access device destroys the cap such that the cap cannot be reused. Said single use caps or covers will help ensure compliance with infection prevention protocols in healthcare settings, which will assist in reducing incidences of healthcare-associated infections (HAIs), particularly catheter-related blood stream infections. Assemblies and kits including said caps or covers, for example, IV administration and extension sets that include one or more needlefree connectors, as well as methods for using said caps or covers, are also described.

16 Claims, 7 Drawing Sheets

Related U.S. Application Data

(60) Provisional application No. 62/940,886, filed on Nov. 27, 2019, provisional application No. 62/938,374, filed on Nov. 21, 2019, provisional application No. 62/933,661, filed on Nov. 11, 2019.

(51) Int. Cl.
*A61M 5/50* (2006.01)
*A61M 5/14* (2006.01)

(52) U.S. Cl.
CPC ....... *A61M 5/14* (2013.01); *A61M 2039/0229* (2013.01); *A61M 2039/205* (2013.01); *A61M 2205/273* (2013.01)

(58) Field of Classification Search
CPC .... A61M 5/5086; A61M 5/14; A61M 5/1413; A61M 2039/0009; A61M 2039/0229; A61M 2039/0258; A61M 2039/027; A61M 2039/0285; A61M 2039/0288; A61M 2039/1016; A61M 2039/1027; A61M 39/0208; A61M 39/0247; A61M 39/10; A61M 39/1011; A61M 39/16; A61M 39/162; A61M 39/165; A61M 39/22; A61M 2205/0238; A61M 2205/27

See application file for complete search history.

(56) References Cited

U.S. PATENT DOCUMENTS

| | | |
|---|---|---|
| 5,226,883 A | 7/1993 | Katsaros et al. |
| 5,531,695 A | 7/1996 | Swisher |
| 7,780,794 B2 | 8/2010 | Rogers et al. |
| 7,985,302 B2 | 7/2011 | Rogers et al. |
| 8,172,825 B2 | 5/2012 | Solomon et al. |
| 8,206,514 B2 | 6/2012 | Rogers et al. |
| 8,523,831 B2 | 9/2013 | Solomon et al. |
| 8,961,475 B2 | 2/2015 | Solomon et al. |
| 9,114,915 B2 | 8/2015 | Solomon et al. |
| 9,809,355 B2 | 11/2017 | Solomon et al. |
| 9,895,526 B2 * | 2/2018 | Korogi ................ A61M 39/165 |
| 10,155,056 B2 | 12/2018 | Solomon et al. |
| 2010/0242993 A1 | 9/2010 | Hoang et al. |
| 2019/0070404 A1 | 3/2019 | Anderson |
| 2020/0197686 A1 | 6/2020 | Anderson et al. |

* cited by examiner

FIG. 5C
FIG. 5D
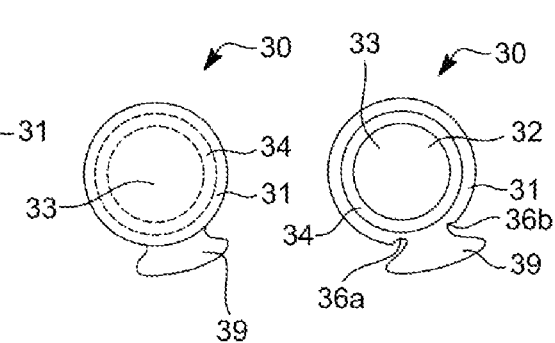

FIG. 5F
FIG. 5G
FIG. 5H
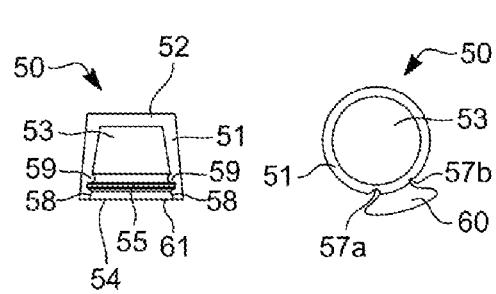

SINGLE USE CAPS AND COVERS FOR VASCULAR ACCESS DEVICES, AND KITS AND METHODS FOR USING THE SAME

RELATED APPLICATIONS

This application is a continuation which claims the benefit of and priority to U.S. bypass continuation under 35 U.S.C. 120, 365(c), and 37 CFR 1.78 patent application Ser. No. 17/115,626, filed 8 Dec. 2020, which claims the benefit of and priority to U.S. international patent application serial no. PCT/US20/60310, filed 12 Nov. 2020, and U.S. provisional patent application Ser. Nos. 62/933,661, filed 11 Nov. 2019, 62/940,886, filed 27 Nov. 2019, and 62/938,374, filed 21 Nov. 2019, each of which is hereby incorporated by reference in its entirety for any and all purposes.

TECHNICAL FIELD OF THE INVENTION

This invention is directed to single use caps for vascular access devices that have one or more ports for introducing fluids into a patient's vasculature, including, for example, vascular access devices such as needlefree, valved connectors as well as connectors where the access or injection site is adapted to receive a needle, and kits containing such devices and methods for using them.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

Healthcare acquired infections (HAIs), i.e., infections that patients acquire while admitted to a hospital or surgery center for another, unrelated reason, are a primary concern in healthcare. Each year in the U.S., more than 100,000 people die from HAIs; many times that number become ill but do not die as a result of an HAI. Among the leading types of HAIs are catheter-related bloodstream infections (CRBSIs), which are infections that arise as a result of a patient having a central venous catheter and/or peripheral intravenous (IV) catheter inserted into a blood vessel, for example, a vein, to deliver hydration, nutrients, and/or medication.

As those in art appreciate, placement of a central line or peripheral IV compromises a patient's natural skin-based barrier against infection by microorganisms found in the environment, be they resident on the patient's skin, in the air, or on a surface that comes into contact with the patient. Indeed, an IV-caused compromise of a patient's skin is not just at the location where a catheter is inserted through the skin (the insertion site), but also at every opening that may be present on the fluid delivery set (typically comprised of a primary IV administration set and often a secondary extension set) used to connect one or more external fluid source(s) to the central line or peripheral IV catheter, as any such opening provides a potential entry point for pathogens into the patient's vasculature.

Prior to the outbreak of the AIDS epidemic in the 1980's, it was common practice to use needles to inject fluids and medicines directly into patients or, alternatively, into access or injection ports included in IV sets adapted to receive needles. When it became clear, however, that inadvertent needle-stick injuries were becoming a major source of HIV transmission between patients and healthcare workers, needlefree connectors (NCs) to provide needlefree (or needleless) vascular access were developed; their use has since become widespread. Indeed, in the U.S. today more than one billion NCs are used annually in healthcare settings in connection with providing peripheral venous and central line vascular access to patients in hospitals, outpatient surgery centers, dialysis centers, long-term care facilities, homes, and home-based healthcare facilities. Most NCs are used in IV sets, which may contain from as few as one to as many as 3, 4, 5, or more NCs. But because NCs serve as fluid access ports, they can also serve as access points for microbial pathogens. Indeed, widespread NC use in acute medicine has contributed to a marked increase in HAI incidence, particularly CRBSIs, because these devices rapidly become contaminated with microorganisms from the surrounding environment when they are removed from their often sterile packaging and placed on a patient to deliver fluids to her/him as part of an IV set, for example. Sources of environmental contamination include a patient's own skin microbiome, bedding, hand transfer from a healthcare worker, etc.

As a result of such problems, in order to reduce the risk of infection from contaminated NCs, standard practice today includes a requirement that, before accessing an NC in an IV set, a healthcare worker must clean the NC surfaces in the IV's fluid flow path by scrubbing those surfaces with a sterile alcohol swab or wipe immediately prior to making a fluid connection to the valve, for example, by attaching a syringe to the valve to deliver a medication via a peripheral IV already connected to a patient. More recently, disinfecting caps (also called "port protectors") have also been developed to provide up to 7 days of alcohol-based passive protection for NCs having luer fittings. Typically, such caps are threaded on to female or male luer fitting promptly after a healthcare worker first "scrubs the hub" of the fitting using an alcohol swab. Such a cap can be left on the connector for up to 7 days unless the connector is used before then to provide vascular access. Examples of such caps include Curos® (3M Corp.), SwabCap (ICU Medical, Inc.), and DualCap® (Merit Medical Systems). See, e.g., U.S. Pat. Nos. 7,780,794; 7,985,302; 8,206,514; 8,172,825; 8,523,831; 8,961,475; 9,114,915; 9,809,355; and 10,155,056. More recently, disinfecting caps that provide active "scrubbing" capability in combination with up to 7 days of capping have also been developed. See, e.g., commonly owned U.S. patent application Ser. Nos. 16/059,029 and 16/795,565.

Despite such advances, however, CRBSIs continue to represent a significant healthcare challenge. And given the magnitude of the mortality and morbidity associated with CRBSIs that result from peripheral IV and central line use, a long-recognized yet significant unmet need remains for articles or devices that can be used to reduce or eliminate the risk of initiating an HAI merely by accessing a patient's vasculature through an NC or other access or injection port adapted to receive a needle that is a component of an IV or other vascular access set connected to a catheter or cannula inserted into a blood vessel of a patient.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

As used herein, the singular forms "a", "an", and "the" include plural references unless the context clearly dictates otherwise.

As used herein, the term "about" refers to approximately a +/−10% variation from the stated value. It is to be understood that such a variation is always included in any given value provided herein, whether or not it is specifically referred to.

The terms "functional attachment", "functional connection", "functional reattachment", "functional reconnection", and the like refer to (re)attachment or (re)connection of or between two or more articles (e.g., a single use cap according to the invention and a needlefree connector) in an intended manner that allows each article to perform its intended function(s).

A "patentable" composition, process, machine, or article of manufacture according to the invention means that the subject matter at issue satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

The terms "removably attached", "removably connected", and the like refer to non-permanent attachment of connection between two or more articles, for example, between articles with complementary threaded regions, between articles in which one is press-fit (i.e., an interference fit between two parts in which one is forced under pressure into or through a slightly smaller hole, bore, cavity, opening, etc. in the other) with another using complementary structures, etc.

The terms "resilient", "resilience", and the like refer to the ability of a material, such as a plastic, to absorb energy when it is elastically deformed. As deformation occurs, intermolecular forces in the material arise that oppose the applied, deforming force, such as occurs when a cap of the invention is advanced onto a vascular access port and moved over the puts retainer. In the context of the invention, the force required to be applied by a user to Install a cap on a vascular access port will be such that it will not overcome the inter-molecular forces of the plastic material (or combination of materials) used to form the cap (particularly its sidewall), allowing the cap to withstand the applied force without damage and to assume a new, lower energy equilibrium state when the load is removed, as occurs when a cap of the invention is advanced sufficiently over a vascular access port so that the port's retainer is in the retaining channel in the cap's sidewall.

A "single use cap" refers to a cap, cover, or protector for an access or injection port of a vascular access device that can only be used once; in other words, it can only be attached one time and removed one time from a vascular access device access or injection port because removal of the cap, cover, or protector from the port physically alters the cap, cover, or protector, or one or more components or sub-assemblies thereof, to as to prevent the cap, cover, or protector from being reattached or reconnected to the same or a different vascular access device access or injection port in a way that would allow the reattached or reconnected cap, cover, or protector to provide substantially the same degree of capping, covering, or protection to the port as compared to the initial attachment or connection.

The term "species", when used in the context of describing a particular compound or molecule species, refers to a population of chemically indistinct molecules.

The term "vascular access port" means a port or valve on a vascular access device configured to provide fluid access to an IV set, catheter, cannula, or other device connected to, or designed for connection to, a patient in order deliver blood products (e.g., blood, plasma, etc.), hydration, nutrients, and/or medication.

SUMMARY OF THE INVENTION

The object of the invention is to provide single use caps (i.e., a cap, cover, or other protector) for vascular access devices that have one or more ports for introducing fluids into a patient's vasculature. Such devices include, for example, needlefree, valved connectors as well as connectors where the access or injection site is adapted to receive a needle. The single use caps of the invention include one or more features that (i) can be used, and advantageously are required, to remove the cap from an access or injection port and, once utilized to remove the cap, render the cap incapable of being functionally reattached or reconnected to the same or a different vascular access port, or (ii) when used and the cap is removed from an access or injection port to which it is attached or connected, prevent the cap from being re-used, i.e., being functionally reattached or reconnected to the same or different vascular access port. Accordingly, use of caps according to the invention in the context of vascular access in healthcare will help ensure compliance with infection prevention protocols that mandate disinfection of vascular access ports immediately prior to vascular access, to the benefit of patients, healthcare providers, hospitals, third party payers, and society in general.

Thus, in one aspect, the invention concerns single use vascular access port caps configured to prevent reuse of the single use cap after the cap has been removed from a vascular access port of a vascular access device. Such single use caps generally are formed to have a hollow cap body that includes an open end and a closed end (or closed region more proximate to one end than the other). The interior of the cap body forms a cavity that can be accessed through the open end. The cap body is formed to have one or more sidewalls that have any desired geometric (or other) cross section. For example, in some preferred embodiments a single sidewall is used to form a cylinder, while in others the sidewall forms a truncated cone (where the top has a slightly smaller diameter than bottom. In others, the sidewalls form, for example, a structure having a polygonal cross section, for example, one having any of 3-12 or more sides of equal or different lengths.

The sidewall(s) of the cap body is(are) adapted to securely receive and retain a vascular access port of the vascular access device to be capped, covered, or protected. Any suitable structures, or combinations of structures, can be used to achieve such secure receipt and retention. Such structures include, for example, complementary threaded regions on the interior surface of a cap's cavity and on the exterior surface of the valve portion of a needlefree connector. Similarly, a single use cap of the invention may be designed to provide an interference fit between the cap and a vascular access port.

In some preferred embodiments that employ an interference fit for cap-access port engagement, the cap body can include a plurality of preferably resilient (i.e., flexible, spring-like) protrusions (e.g., 2-12 or more) extending from the sidewall's interior surface that are adapted to engage, for example, threads, thread tabs, or a collar or flange or the like on a vascular access port so as to prevent removal of the cap after it has been installed on a vascular access device in order to cap, cover, or otherwise protect a vascular access port. In some of these embodiments, such (flexible) protrusions extend toward the closed end wall of the cap body. As the cap is pushed onto a vascular access port, the protrusions are pushed radially outward toward the circumference that bounds the corresponding inner surface of the cavity to as to allow features on the exterior surface of vascular access port, for example, threads or thread tabs, to push past the protrusions. Once a feature on the exterior surface of vascular access port clears a protrusion, the protrusion rebounds (partially or, preferably, completely (or nearly so)) into a position that prevents removal of the cap from the vascular access port until after separating region in the cap body is activated.

In still other preferred embodiments that employ an interference fit for cap-access port engagement, the cap body can include a circumferential channel formed into the inner surface of the sidewall that is designed to engage a collar, flange, thread tabs, or similar structure(s) on the neck of vascular access port. For many threaded vascular access ports, structures such collars or flanges are found below the port's threaded region and can be engaged by a circumferential channel in the cap's sidewall near the cap's opening as the cap is press-fit onto the access port.

As the hollow cap body is closed at (or near) one end (the closed end), it forms a cavity sufficiently sized and configured to receive a vascular access port of a vascular access device to be capped, covered, or protected. The interior surface(s) formed by the sidewall(s) of the cavity (or by another element inserted into the cavity during manufacture to provide the desired surface features, size, shape, etc.) can have the same or different cross section as the corresponding exterior surface(s) of the cap. For example, when taken in circumferential cross section, the exterior of the single use cap's body may have a hexagonal cross section while the interior surface defines a circle. In many preferred embodiments, the cap body is substantially cylindrical, with the majority of the interior and exterior surfaces of the sidewall having concentric circular cross sections. In other preferred embodiments, the cap body, when viewed from the side, has a slight conical shape that is truncated at the top (which is closed). The outer diameter of the sidewall decreases slightly from the bottom of the cap to the top, closed end. Preferably, the inner diameter of the sidewall also correspondingly decreases from its bottom (which defines the sidewall's first or lower edge) to top (capped by the closed end wall).

The opening in, or open end of, the body opposite the closed end is defined by the lower edge of the sidewall(s) or any extension thereof or lower element(s) connected thereto (e.g., flanges, collars, pull tabs, and the like). The opening is sized to allow the single use cap to be placed over and advanced on to the vascular access port during assembly of IV sets, etc. such that at least a needlefree valve portion or injection portion of the vascular access port will be disposed inside the cavity when the cap is removably attached to the vascular access port.

The single use caps of the invention also include one or more features that is/are required to remove the cap from a vascular access port and/or which, when the cap is removed from the vascular access port, render it incapable of reuse. In other words, in some embodiments removal of a single use cap according to the invention destroys or otherwise prevents the cap, once removed from a vascular access port, from being functionally reattached or reconnected to the same or different port. In some preferred embodiments, this is accomplished by providing a cap body that includes at least one separating region in the cap body, optionally a tear strip bounded by two spaced tearable regions (e.g., curved or straight seams or thinned regions (e.g., channels or grooves) in the sidewall) extending at least from the first edge of the sidewall toward, and optionally into, the closed end wall of the cap.

To facilitate separation of the separating region of a single use cap of the invention in order to effect its removal, the cap also preferably includes one or more pull tabs connected to a sidewall portion proximate to the first, or lower, edge of the sidewall. Such pull-tabs are configured for grasping by a user and optionally can include one or more grip-enhancing elements. When pulled with sufficient force, the pull tab(s) transfers separating force to the seam(s) formed in separating region in the sidewall (which, in some embodiments, may extend into the closed end), causing the seam(s) to break or rupture and thereby allow adjacent regions of the sidewall to separate. Such separation reduces the capping forces applied by the cap, which allows the user to remove the cap from the vascular access port while at the same time rendering the cap unsuitable for subsequent use as a cap, cover, or protector for the same or another vascular access port.

In some embodiments, the single use caps of the invention employ two pull tabs, preferably in configurations where one pull tab is located on either side of a single separating region, preferably a separating seam, in the sidewall. Such a configurations allows a user to use both pull tabs to break or otherwise pull apart the separating seams to facilitate subsequent removal of the cap from the capped vascular access port.

In other preferred embodiments, the separating region is a tear strip bounded by two spaced tearable regions at least one of which (and preferably both) extend at least from the first edge of the sidewall toward, and optionally into, the cap's closed end wall. Preferably, a pull tab connected to the tear strip proximate to the first edge of the sidewall is included so that when the pull tab is grasped and pulled by a user the tear strip tears along its seams, causing the cap's sidewall (and optionally, closed top) to separate along at least a portion of its height, facilitating removal of the cap from the vascular access port and rendering the cap unsuited for further use as a cap, cover, or protector for the same or another vascular access port. The tear strip can be of any suitable size, length, and orientation from the sidewall, for example, projecting downward below the first edge of the sidewall. Other pull-tab configurations include projecting outward from the sidewall (optionally substantially perpendicular to the sidewall) or outward and upward (in a "V"- or "U"-shaped configuration).

In yet other preferred embodiments, the separating region is a tear strip bounded by a curved tearable region that extends upward at least from the first (bottom or lower) edge of the sidewall and then curves toward the first edge, optionally until it is substantially parallel with the first edge, to form tear strip that extends at least partially around the circumference of the sidewall. Preferably, a pull tab connected to the tear strip proximate to the first edge of the sidewall is included so that when the pull tab is grasped and pulled by a user the tear strip tears along its seams, causing the cap's sidewall (and optionally, closed top) to separate along at least a portion of its height, facilitating removal of the cap from the vascular access port and rendering the cap unsuited for further use as a cap, cover, or protector for the same or another vascular access port.

In some preferred embodiments, a single use cap of the invention further includes one or more vents. Such vents can be formed in the sidewall(s) or the closed end. Such caps also preferably also include a gas-permeable barrier associated with any vent in order to allow gas but not microorganisms to pass through the associated vent(s).

In some preferred embodiments, a single use cap of the invention that is secured to a vascular port other than by threading further includes a port-engaging element configured to engage the needlefree valve portion or injection portion of a vascular access port. Such port-engaging elements include any suitable matrix, for example, a compressible medical grade foam. The port-engaging element(s) advantageously interface with at least the outer surface of a valve disposed in the vascular access port to provide fluid access. In some embodiments, the port-engaging element is also designed to contact non-valve surfaces of the vascular access port, for example, those adjacent to the outer surface of the valve, portions of threaded region of the vascular access port, etc. Preferably, such port-engaging elements optionally also provide continuing antimicrobial action when the cap is attached to a vascular access port. Antimicrobial action can be provided by any suitable liquid or other an antimicrobial agent, for example, 70% isopropyl alcohol, chlorhexidine, silver ions, or the like.

In some preferred embodiments, particularly those that include a port-engaging element, a single use cap of the invention further includes a removable or peelable seal that covers the open end of the cavity. Generally, such a seal is installed during manufacture of the cap, prior to sterilization. The seal is then removed by a user immediately prior to placing the cap on a vascular access port to be capped, covered, or otherwise protected.

A single use cap of the invention is designed to cap, cover, or protect one or more exterior surfaces of a vascular access port of a vascular access device to which the cap can be attached, for example, the exterior surfaces of a female threaded valve portion of a needlefree connector, a Y-site that includes a needlefree connector portion having a female threaded valve portion, a Y-site having a needle injection port, a T-site that includes a needlefree connector portion having a female threaded valve portion, a T-site having a needle injection port, an open female luer region such as found on a central line or catheter, or similar vascular access device. Such surfaces can include threaded regions, the exterior surfaces of the valve (or plunger) portion of the needlefree connector, needle injection sites, etc.

A related aspect of the invention relates to assemblies that comprise a single use cap according to the invention attached to a vascular access port of a vascular access device. Some of these embodiments of this aspect include vascular access devices that are part of an IV set, for example, a primary IV administration set, a secondary IV administration set, an IV extension set, a needlefree connector, a central line, or a vascular access connector that comprises a needle injection port.

Yet another related aspect of the invention involves kits that include an assembly according to invention packaged in a sealed container. Such kits preferably are sterilized. Sterilization can be achieved using any suitable process, including by gamma irradiation, use of an electron beam, or by a sterilizing gas such as ethylene oxide. Preferably, sterilization of the lumens of all tubing, connectors, and/or fittings that form a part of the fluid path of any such device or assembly is maintained until devices or assemblies become filled with the desired fluid(s) (e.g., IV fluid, medication, blood, etc.) during use, and advantageously the surfaces of the vascular access ports protected by a single use cap according to the invention do not become contaminated with microorganisms, and preferably remain sterile until the cap is removed.

Still other aspects of the invention concern various methods. For example, one such aspect relates to methods of capping, covering, or protecting vascular access ports of vascular access devices. Such methods include attaching a single use cap according to the invention to a desired vascular access port, thereby capping, covering, or protecting it. Another related aspect concerns methods of uncapping, uncovering, or de-protecting vascular access ports of vascular access devices capped, covered, or protected with a single use cap according to the invention. In such methods, a user separates the one or more separating region(s) of a cap according to the invention, for example, by pulling a pull tab to tear a separating seam in the cap's sidewall (which seam(s) in some embodiments extend into the closed end cover). This relieves retention force applied by the cap's sidewall to the vascular access device, thereby facilitating the user's ultimate removal of the cap from the vascular access device to thus uncap, uncover, or de-protect the vascular access port.

These and other aspects and embodiments will now be described in detail with reference to the accompanying drawings and the descriptions below. Other features and advantages will be apparent from the description and drawings, and from the appended claims.

BRIEF DESCRIPTION OF THE DRAWINGS

Unless otherwise indicated, it is understood that the drawings are not to scale, as they are intended merely to facilitate understanding of the invention as opposed to specific dimensions, etc. In the drawings, like numbers in two or more drawings represent like elements. The illustrative embodiments described herein are not meant to be limiting. Other embodiments may be utilized, and other changes may be made, without departing from the spirit or scope of the subject matter presented here.

FIGS. 1-7 depict various views and embodiments of single use caps according to the invention.

FIGS. 1 and 2 are illustrations of IV sets whose Y-site connectors that can be protected using a single use cap according to the invention.

FIGS. 5A-5H shows four views of each of two representative embodiments of a single use cap according to the invention. Views A-D illustrate one embodiment of a single use cap that threads onto the complementary luer threads of the threaded female portion of a vascular access port of, for example, an NC, Y-site, or the like. Views E-H illustrate one embodiment of a single use cap configured to be press-fit onto a threaded female portion of a vascular access port of, for example, an NC, Y-site, or the like, wherein retention of the cap is accomplished by a circumferential groove that is complementary to a collar or flange below the threaded region of the vascular access port.

FIG. 7 shows yet another representative embodiment of a single use cap of the invention secured to a vascular access port and including a port-engaging element configured to engage the needlefree valve portion or injection portion of a vascular access port so as to facilitate active mechanical friction, or "scrubbing" of adjacent port surfaces.

A more complete understanding can be obtained by reference to the following descriptions of specific embodiments of the invention, which are provided herein for purposes of illustration only and are not intended to limit the scope of the invention.

DETAILED DESCRIPTION OF THE INVENTION

Figure 1:
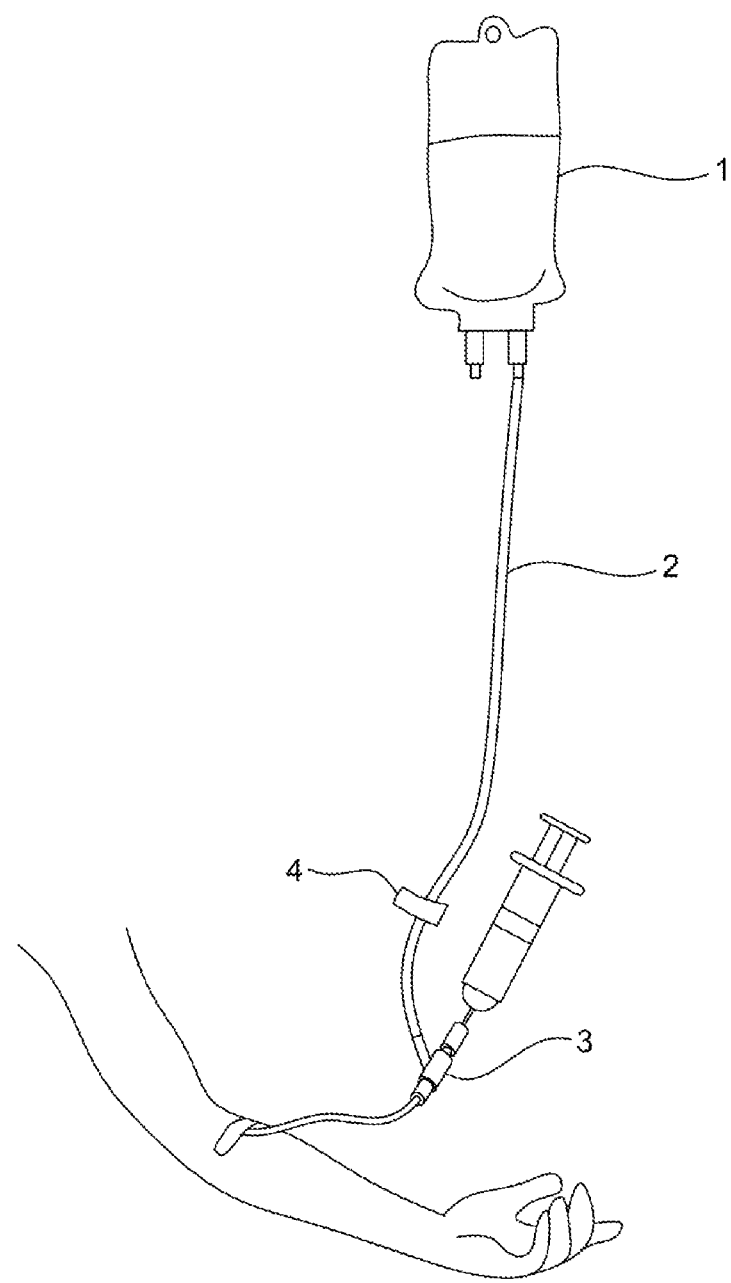

FIG. 1 is an illustration that shows an IV set with a single Y-site connector (3) attached to a patient. The IV set includes an IV bag (1) containing IV fluids connected to the patient via a primary IV set, a Y-site vascular access port (3) to which a syringe is attached. A clamp (4) is also included to allow a healthcare worker to control fluid flow into the patient from the IV bag. The primary IV set (2) is connected to the IV bag via a spike and to the catheter hub of an IV catheter inserted into a vein in the patient's arm.

Figure 2:
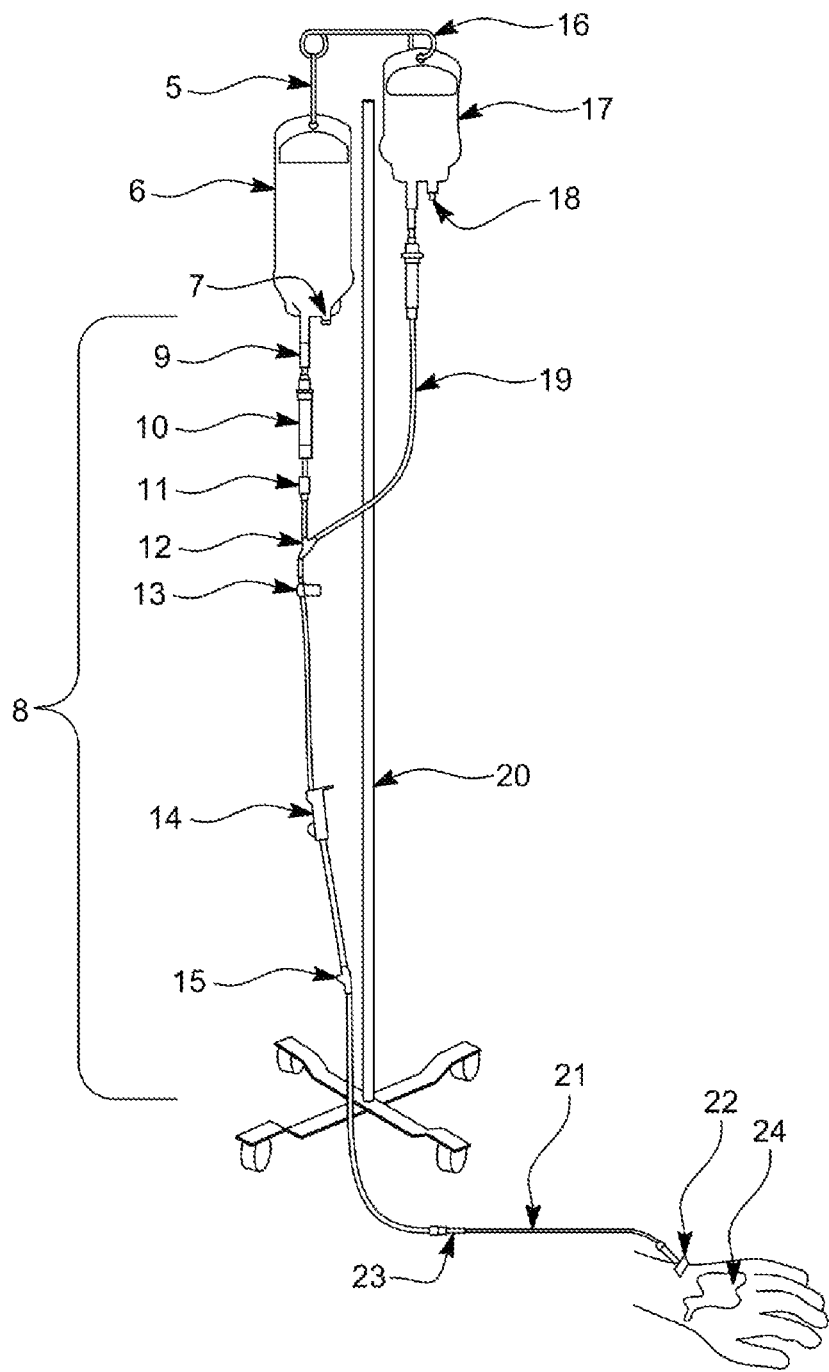

FIG. 2 is an illustration showing an IV set with two threaded luer-type Y-site connectors (12, 23) attached to a patient via an extension set (21). The IV set also includes a secondary IV medication set attached to the primary IV set the most distal Y-site (12). The primary IV bag (6) is hung from the IV pole (20) via a bag hanger (5). The IV bag contains an auxiliary fluid access port (7) to facilitate the addition of other fluids and medications directly into the IV bag (6). The primary IV administration set (8) is connected to the primary IV bag via a spike (9) and to the patient via an extension set (21) connected via a luer fitting to a catheter inserted into a vein on the back of the patient's hand. The primary IV and extension sets are connected via complementary connectors having luer fittings (23). The arrangement shown also includes a secondary IV (17) hung from the IV pole (20) via a loop (16). The secondary IV bag also includes an auxiliary fluid access port (18). The IV also includes two clamps (13, 22) to start and stop fluid delivery as well as a roller clamp (14) to control the rate of fluid delivery to the patient. In the configuration shown, the Y-site closest to the patient is unprotected, leaving its vascular access port exposed to the environment and susceptible to microbial contamination.

Figure 3A:
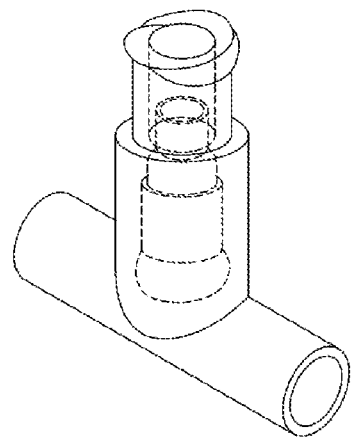
FIGS. 3A-3C illustrates three representative vascular access connector types (A-C)-whose vascular access ports can be protected using a single use cap according to the invention.
Figure 3B:
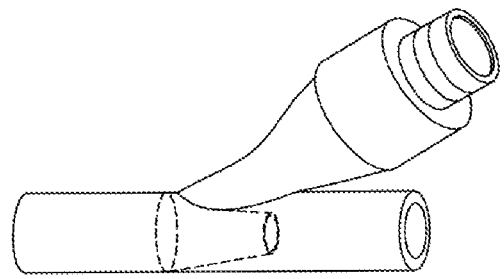
Figure 3C:
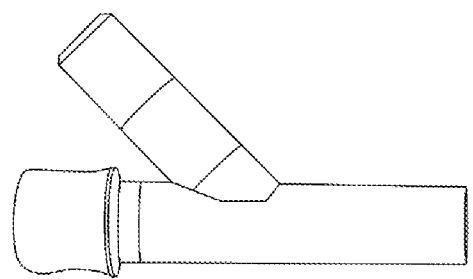
Figure 4A:
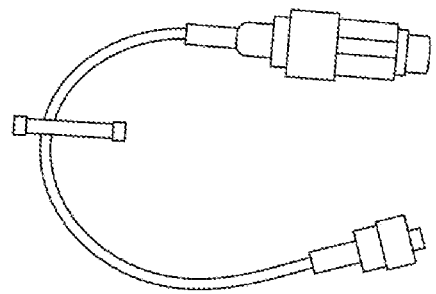
FIGS. 4A-4D illustrates four representative types of IV sets (A-D) having vascular access connectors whose vascular access ports can be protected using a single use cap according to the invention.
Figure 4B:
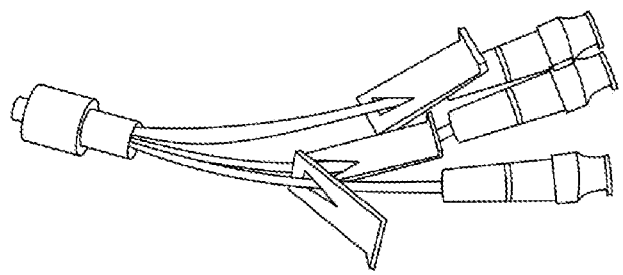
Figure 4C:
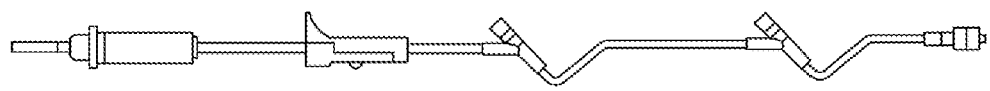
Figure 4D:
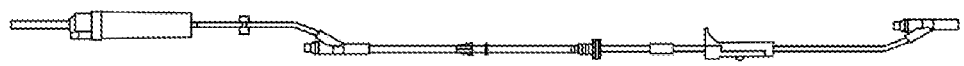

FIG. 3 shows three connectors, (A) a T-site having a vascular access port with luer thread tabs, wherein the access port includes a valve (shaded region) in the vascular access port, (B) a Y-site having a threaded vascular access port that contains a vascular access valve (shaded region), and (C) a Y-site having an injection port. The connectors of these devices have three branches, one of which is the vascular access port and the other two are configured for connection with a desired length of IV tubing (not shown).

FIG. 4 shows (A) an extension set having an unprotected single vascular access port, (B) an extension set having a three unprotected vascular access ports with thread tabs for connection to complementary threaded male luer fittings, (C) an IV set having two unprotected Y-site connectors with an injection ports, and (D) an IV set having two unprotected Y-site connectors each having a threaded vascular access port. Each of the vascular access ports shown in this Figure can be capped and protected by a suitably configured single use cap according to the invention.

As described, this invention concerns single-use disinfecting caps or covers for vascular access devices (e.g., needlefree connectors) as are found, for example, intravenous administration sets, extension sets, and needlefree connectors. Such caps can be threaded or snap-fit onto the vascular access ports of vascular access devices and provide for both active disinfection of valve surfaces via rotation of the cap in relation to the capped or covered valve as well as passive capping. Removal of a single-use cap or cover according to the invention destroys the cap such that it cannot be reused. This will help ensure compliance with infection prevention protocols in healthcare settings, which in turn will help reduce the incidence of healthcare-associated infections (HAIs), particularly catheter-related blood stream infections.

Figure 5A:
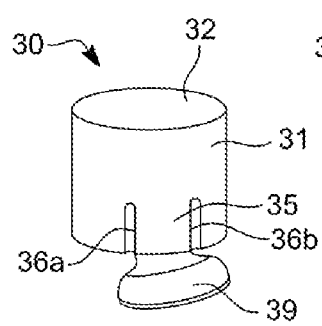
Figure 5B:
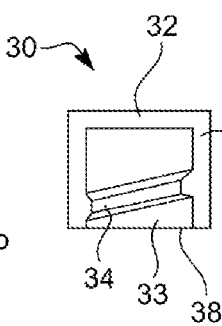
Figure 5E:
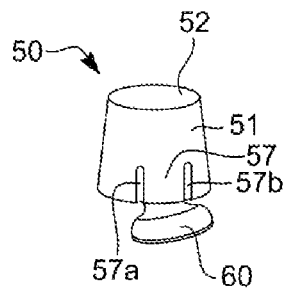

FIG. 5 shows four views of each of two representative embodiments of a single use cap according to the invention. Views A-D illustrate one embodiment of a single use cap that threads onto the complementary luer threads of the threaded female portion of a vascular access port of, for example, an NC, Y-site, or the like.

With reference to FIG. 5, some embodiments of the invention concern thread on or press-fit or snap-fit, single-use vascular access port caps configured to cap and protect the vascular access ports of various types of vascular access devices and to prevent the cap's reuse after removal from a vascular access port to which it had previously been connected (or to another such port on a different vascular access device). Such caps typically include a cap body made of a resilient plastic that forms a sidewall that, with a closed end, forms a cavity that can be accessed from an open end opposite the closed end; one or more retaining elements that allow the cap to be retained or removably secured to a vascular access port; at least one separating region configured to allow the sidewall to be separated as so to allow the cap to be removed from the vascular access port to which it has been attached and to prevent the cap's functional reattachment to the same or different vascular access port; and a pull (or removal) tab connected to a portion of the sidewall proximate to the first edge of the sidewall and at least one separating region, which pull tab is configured for grasping by a user and, when pulled with sufficient force, causes the sidewall to separate in at least a portion of the separating region so as to allow the user to then remove the cap from the vascular access port.

FIG. 5, views A-D, illustrate an embodiment of the invention wherein the single use cap is configured to be threaded onto a threaded female portion of a vascular access port of, for example, an NC, Y-site, T-site or the like. In this embodiment, the cap body of the cap (30) is preferably substantially cylindrical (or a truncated slightly tapered cone) and has a sidewall (31) that, with a closed end wall (32), forms a cavity (33) accessible from an open end (38) opposite the closed end wall (32). The sidewall (31) (*i*) is configured to cover a threaded valve portion of a vascular access port of a vascular access device to which the cap (30) is attached, (ii) includes threads (34) configured for engagement of complementary threads disposed on the exterior surface of the vascular access port, and (iii) includes at least one sidewall separating region (35) configured to allow separation of at least a portion of the sidewall (31), wherein the sidewall separating region (35) is optionally a tear strip bounded by two spaced tearable regions (36*a*, 36*b*) in the sidewall (31).

In the embodiment shown in FIG. 5, views A-D, the cap (30) also includes a pull or removal tab (39) configured for grasping by a user. When pulled with sufficient force, the pull-tab (39; here, the pull-tab is directed outward from the cap body) causes the sidewall to separate along at least a portion of the tearable region(s) (36*a*, 36*b*). This allows the user to then easily remove the cap (30) from the vascular access port. Such separation also prevents re-use of the cap (30) as it is no longer suitable for secure attachment to and protection by a vascular access port, be it the port previously protected by the cap or a different vascular access port on a different vascular access device.

In some embodiments of this sort, a thread-on cap of the invention includes only one separating region formed in the sidewall. For example, the separating region can be a groove or channel that begins at the open, lower edge of the sidewall and then curves so as to become substantially parallel with the sidewall's lower edge at a position above the retaining channel so that when the separating region is activated by a user applying sufficient pulling force to the pull or removal tab (39), the sidewall separates at least in part along the separating region, allowing the user to remove the cap from the vascular access port to which it had been attached.

With reference to FIG. 5, views E-H, an embodiment is illustrated that shows a single use cap configured to be press-fit onto a threaded female portion of a vascular access port of, for example, an NC, Y-site, T-site or the like, wherein retention of the cap is accomplished by a circumferential groove that is complementary to a collar or flange below the threaded region of the vascular access port. In this embodiment, the cap body of the cap (50) is preferably substantially cylindrical (or a truncated slightly tapered cone) and has a sidewall (51) that, with a closed end wall (52), forms a cavity (53) accessible from an open end (54) opposite the closed end wall (52). The sidewall (51) (*i*) is configured to cover a threaded valve portion of a vascular access port of a vascular access device to which the cap (50) is attached, (ii) includes a retaining channel (55) configured for snap-fit engagement of a retaining element (e.g., a collar or flange) disposed on a first region of the exterior surface of the vascular access port below its threaded valve portion, wherein the retainer is optionally a collar or a plurality of circumferentially arrayed, spaced retaining elements, and (iii) includes at least one sidewall separating region (56*a*, 56*b*) configured to allow separation of at least a portion of the sidewall (51) in which a portion of the retaining channel (55) is formed, wherein the sidewall separating region (56) is optionally a tear strip bounded by two spaced tearable regions (57*a*, 57*b*) in the sidewall (51). In many embodiments, inner surface (58) of the sidewall in the region extending upward from the lower edge (60) (which forms the open end (54) of the cap (50)) to the retaining channel is inwardly tapered over at least a portion of its length so as to facilitate press- or snap-fit engagement of the cap (50) with a vascular access port of a vascular access device.

In many preferred embodiments, the sidewall also includes a fluid seal (59) configured to engage a second region of the exterior surface of the vascular access port below its threaded valve portion, wherein the second region of the exterior surface of the vascular access port is optionally disposed between the threaded valve portion and the first region (i.e., retaining element) of the exterior surface of the vascular access port. In other words, in some preferred embodiments, the fluid seal (59) formed on the interior surface of the sidewall (51) is disposed further into the interior of the cap (50) than the retaining channel (55). In some preferred embodiments, and as shown in FIG. 5F, the fluid seal (59) forms the upper portion of the cap's retaining element (55).

In some embodiments, the cap of the invention includes only one separating region formed in the sidewall. For example, the separating region can be a groove or channel that begins at the open, lower edge of the sidewall and then curves so as to become substantially parallel with the sidewall's lower edge at a position above the retaining channel so that when the separating region is activated by a user applying sufficient pulling force to the pull or removal tab (60), the sidewall separates at least in part along the separating region, allowing the user to remove the cap from the vascular access port to which it had been attached.

In the embodiment shown in FIG. 5, views E-H, the cap (50) also includes a pull or removal tab (60) configured for grasping by a user. When pulled with sufficient force, the pull-tab (60) causes the sidewall to separate along at least a portion of the tearable region(s) (57*a*, 57*b*). This allows the user to then easily remove the cap (50) from the vascular access port. Such separation also prevents re-use of the cap (50) as it is no longer suitable for secure attachment to and protection by a vascular access port, be it the port previously protected by the cap or a different vascular access port on a different vascular access device.

Figure 6A:
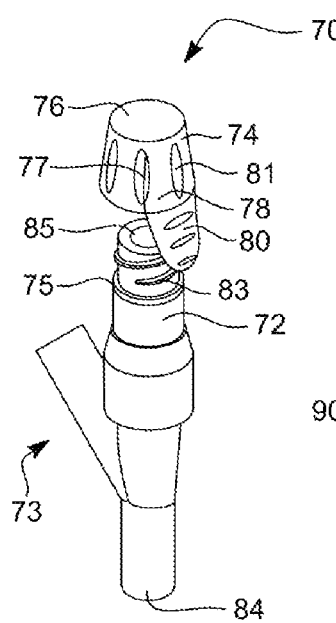
FIGS. 6A-6C shows three views of an embodiment of a single use cap according to the invention prior to assembly with (A), assembled with (B), and after removal from (C) a Y-site.
Figure 6B:
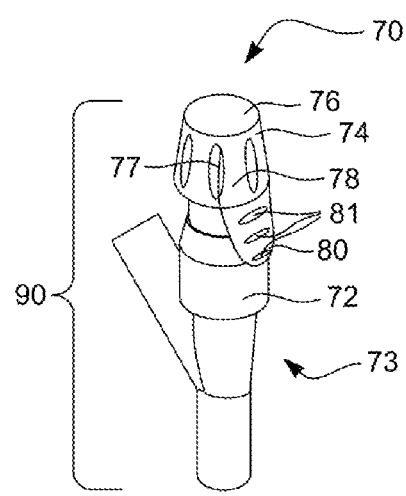
Figure 6C:
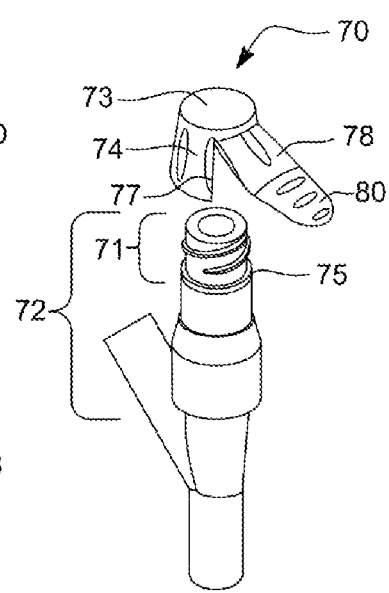

With reference to FIG. 6, views A-C, an embodiment of the invention is illustrated that shows a single use cap (70) configured to be press-fit onto a threaded female portion (71) of a needlefree vascular access port (72) of Y-site connector (73) wherein retention of the cap is accomplished by a circumferential groove (not shown, but see FIG. 5, views E-H, retaining channel (55), for an analogous structure) formed in the cap's sidewall (74) that is complementary to a collar (75) or flange below the threaded region (71) of the vascular access port (72). View 6A shows the cap (70) and Y-site (73) prior to assembly. View 6B shows the cap (70) and Y-site (73) assembled into a capped vascular access device (90) wherein the device's vascular access port (72) is protected by cap (70). View 6C shows the assembly after the cap has been destructively removed by using the pull tab (80) to tear open the separating region (77) in the cap's sidewall (74).

In the embodiment shown in FIG. 6, the cap body of the cap (70) is a truncated slightly tapered cone having a sidewall (74) that, with a closed end wall (76), forms a cavity accessible from an open end opposite the closed end wall (76). The sidewall (74) (*i*) is configured to cover the threads (83) a threaded valve portion (71) of a vascular access port of a vascular access device (here, a Y-site) to which the cap (B) is attached, (ii) includes a retaining channel (not shown) configured for snap-fit engagement of the access port's retaining element (75) disposed on a first region of the exterior surface of the vascular access port below its threaded valve portion (71), wherein the retainer (75) is optionally a collar (or, optionally, a plurality of circumferentially arrayed, spaced retaining elements (not shown), and (iii) includes at least one sidewall separating region (77) configured to allow separation of at least a portion of the sidewall (74) in which a portion of the retaining channel is formed, wherein the sidewall separating region (77) is optionally a tear strip bounded by two spaced tearable regions (77) in the sidewall (74). In many embodiments, the inner surface of the sidewall (74) in the region extending upward from its lower edge (which forms the open end of the cap) to the retaining channel is inwardly tapered over at least a portion of its length so as to facilitate press- or snap-fit engagement of the cap (70) with a vascular access port (72) of a Y-site (73) vascular access device. The fluid outlet (84) of the Y-site is designed to be attached to IV suitable tubing (not shown) during the assembly of an IV set, for example. The valve surface (85) of the Y-site's vascular access port (72).

In some embodiments, the sidewall of the cap shown in FIG. 6 also includes a fluid seal configured to engage a second region of the exterior surface of the vascular access port below its threaded valve portion, wherein the second region of the exterior surface of the vascular access port is optionally disposed between the threaded valve portion and the first region (i.e., retaining element) of the exterior surface of the vascular access port. In other words, in some preferred embodiments, the fluid seal formed on the interior surface of the sidewall is disposed further into the interior of the cap than the retaining channel. In some preferred embodiments, the fluid seal forms the upper portion of the cap's retaining element.

In some embodiments, the cap of the invention includes only one separating region formed in the sidewall. For example, the separating region can be a groove or channel that begins at the open, lower edge of the sidewall and then curves so as to become substantially parallel with the sidewall's lower edge at a position above the retaining channel so that when the separating region is activated by a user applying sufficient pulling force to the pull or removal tab, the sidewall separates at least in part along the separating region, allowing the user to remove the cap from the vascular access port to which it had been attached.

In the embodiment shown in FIG. 6, the cap (70) also includes a downwardly directed pull or removal tab (80) configured for grasping by a user. Optionally, the pull-tab (81) in this (and other embodiments) can include one or more grip-enhancing features or structures (81); the same is also the case for the exterior surface of the sidewall (74). When pulled with sufficient force, the pull-tab (80) causes the sidewall to separate along at least a portion of the tearable region(s) (77). This allows the user to then easily remove the cap (70) from the vascular access port. Such separation also prevents re-use of the cap (70) as it is no longer suitable for secure attachment to and protection by a vascular access port, be it the port previously protected by the cap or a different vascular access port on a different vascular access device.

Figure 7:
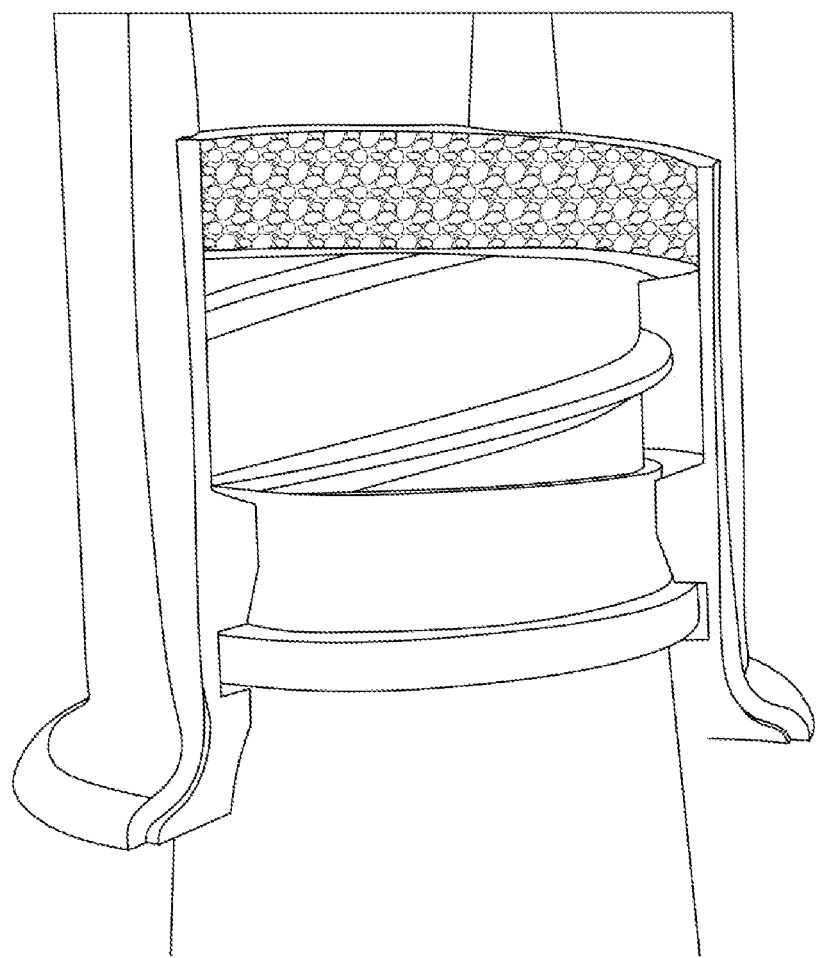

FIG. 7 shows another representative embodiment of a single use cap of the invention that is secured to a vascular port other than by threading further includes a port-engaging element configured to engage the needlefree valve portion or injection portion of a vascular access port. In this and similar embodiments, when securely attached to a vascular access port, the cap can be rotated by a user in relation to the access port. Such port-engaging elements include any suitable matrix, for example, a compressible medical grade foam. The port-engaging element(s) advantageously interface with at least the outer surface of a valve disposed in the vascular access port to provide fluid access. In some embodiments, the port-engaging element is also designed to contact non-valve surfaces of the vascular access port, for example, those adjacent to the outer surface of the valve, portions of threaded region of the vascular access port, etc. Preferably, such port-engaging elements optionally also provide continuing antimicrobial action when the cap is attached to a vascular access port. Antimicrobial action can be provided by any suitable liquid or other an antimicrobial agent, for example, 70% isopropyl alcohol, chlorhexidine, silver ions, or the like. As will be appreciated, when the cap is rotated in relation to a vascular access port to which it is attached, the port-engaging element can be used to "scrub" adjacent surfaces of the access port, including, for example, the valve surface and/or other portions of the exterior of the vascular access port in contact with the port-engaging element. The port-engaging element can be made of one of several parts, of the same or different materials.

In the embodiment shown in FIG. 7, the separating region has been removed from the cap to provide a better view of the cap's interior and the interaction of the port-engaging element (here, a medical grade foam impregnated with a 70% IPA disinfecting solution) with the upper surfaces of the vascular access port of the vascular access device, which surfaces include the exterior surface of face of the valve house in the vascular access port. In this embodiment, the cap body is elongated so as to accommodate the foam insert. Preferably, the foam insert abuts the inner surface of the closed end wall, and in some embodiments the inner surface of the sidewall that contacts the foam insert includes one or more features designed to engage and preferably assist in retention of and prevent rotation (or slippage) of the port-engaging element when the cap is rotated.

When press-fit onto the threaded female portion of the vascular access port the cap is retained by a circumferential groove that is complementary to a collar or flange below the threaded region of the vascular access port. In this embodiment, the cap body is preferably substantially cylindrical (or a truncated slightly tapered cone) and has a sidewall that, with a closed end wall, forms a cavity accessible from an open end opposite the closed end wall. The sidewall (i) is configured to cover a threaded valve portion of a vascular access port of a vascular access device to which the cap is attached, (ii) include a retaining channel configured for snap-fit engagement of a retaining element (e.g., a collar or flange) disposed on a first region of the exterior surface of the vascular access port below its threaded valve portion, wherein the retainer is optionally a collar or a plurality of circumferentially arrayed, spaced retaining elements, (iii) includes at least one sidewall separating region configured to allow separation of at least a portion of the sidewall in which a portion of the retaining channel is formed, wherein the sidewall separating region is optionally a tear strip bounded by two spaced tearable regions in the sidewall, and (iv) accommodate and retain the port-engaging element in the cavity opposite the opening. In many embodiments, inner surface of the sidewall in the region extending upward from the lower edge (which forms the open end of the cap) to the retaining channel is inwardly tapered over at least a portion of its length so as to facilitate press- or snap-fit engagement of the cap with a vascular access port of a vascular access device.

Preferably, the sidewall also includes a fluid seal configured to engage a second region of the exterior surface of the vascular access port below its threaded valve portion, wherein the second region of the exterior surface of the vascular access port is optionally disposed between the threaded valve portion and the first region (i.e., retaining element) of the exterior surface of the vascular access port. In other words, the fluid seal is preferably formed on the interior surface of the sidewall disposed further inside the interior of the cap than the retaining channel. Advantageously, and as shown in FIG. 7, the fluid seal forms the upper portion of the cap's retaining channel.

In the embodiment shown in FIG. 7, the cap's pull or removal tab has been used to remove the separating region. At this point a user can easily remove the cap from the vascular access port. As will be appreciated, such separation also prevents re-use of the cap as it is no longer suitable for secure attachment to and protection by a vascular access port, be it the port previously protected by the cap or a different vascular access port on a different vascular access device.

OTHER CONSIDERATIONS

The instant invention also includes methods for making and using the single use caps and covers described herein. The caps and covers of the invention can be made of any suitable material or combination of materials. In some embodiments, a cap or cover comprises a thermoplastic resin. Such caps and covers can also include metal, ceramics, fibers, resins, and/or other suitable materials, such as waxes and other polymers.

In other embodiments, materials such as cold- or heat-shrinking thermoplastics can be used to cap or cover a vascular access port (or injection site) of a vascular access device, particularly those that are incorporated into IV sets. As is known in the art, heat-shrink materials are typically shrinkable plastic tubes made by an extrusion process.

The single use caps and covers of the invention can be made using any suitable process, or combination of processes. Particularly preferred are injection-molding processes that utilize a thermoplastic resin (or combination of such resins). For other cover materials, different processes are preferred. For example, for waxes and certain polymers, dipping or spray-coating can be used to apply the single use cover, preferably in combination with a tear strip or other material configured for easy removal of the associated cover.

In some embodiments, the caps and covers of the invention are preferably individually sealed and sterilized in suitable packaging. In some of these embodiments, a plurality of caps (e.g., 2-20 or more) are aligned and sealed adjacent to one another on a single foil strip that can be hung, for example, from an IV pole. In this way a user, for example, a nurse, can remove one cap at a time from the strip immediately prior to connecting the cap to a vascular access port on, for example, an IV set connected to peripheral IV or central line in order to provide intravenous fluids, nutrition, and/medication to a hospitalized patient. In other embodiments, a single use cover of the invention is attached to each uncovered vascular access port on an IV set (e.g., a primary or secondary IV administration set) or other vascular access device (e.g., an NC) prior to packaging and sterilization.

After packaging, the sealed caps and covers of the invention (or devices or assemblies to which such caps and and/covers are connected or otherwise attached, e.g., vascular access ports on IV sets) are preferably sterilized using a sterilization method compatible with the materials used to make the single use caps and covers. Examples of such methods include gamma irradiation, e-beam bombardment, and ethylene oxide gas exposure.

Unless the context clearly requires otherwise, throughout the description above and the appended claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list.

The foregoing description, for purpose of explanation, has been described with reference to specific embodiments. However, the illustrative discussions above are not intended to be exhaustive or to limit the invention to the precise forms disclosed. Many modifications and variations are possible in view of the above descriptions. The embodiments were chosen and described in order to best explain the principles of the invention and its practical applications to thereby enable others skilled in the art to best utilize the invention and various embodiments with various modifications as are suited to the particular use contemplated. As such, the invention extends to all functionally equivalent structures, methods, and uses, such as are within the scope of the appended claims, and it is intended that the invention be limited only to the extent required by the applicable rules of law.

The above disclosure generally describes the present invention. All references, patents, and patent applications disclosed herein are expressly incorporated by reference.

What is claimed is:

1. A vascular access assembly, comprising:
   a. a needlefree connector that comprises a vascular access port that comprises a valve region that comprises a valve surface, exterior threads, and a collar disposed below the exterior threads; and
   b. a single use cap removably attached to the valve region of the vascular access port, the cap being configured to (i) be snap fit to the collar of the valve region without threading onto the exterior threads and (ii) be destroyed upon removal so as to prevent reuse of the cap, the cap comprising:
      i. a cap body comprised of a plastic, wherein the cap body comprises a sidewall integrated with a closed end wall, wherein the sidewall and the closed end wall form a cavity, wherein the sidewall and the closed end wall are configured to cover the valve surface, the exterior threads, and the collar of the valve region of the vascular access port upon snap fitting the cap to the collar;
      ii. an opening defined by a first edge of the sidewall and opposite the closed end wall, wherein the opening is sized to allow the cap to be placed over the valve region such that at least the valve surface, the exterior threads, and the collar of the valve region are disposed inside the cavity when the cap is removably attached via the snap fit to the valve region;
      iii. a circumferential channel formed into an interior surface of the sidewall of the cap, wherein the channel is configured to matingly snap fit to the collar on the valve region so as to allow the cap to be retained on the vascular access port;

iv. at least one separating region in the cap body configured to allow the sidewall to be separated so as to allow the cap to be removed from the valve region of the vascular access port to which the cap has been attached and to prevent functional reattachment of the cap to the same valve region or a valve region of a vascular access port of a different needlefree connector; and v. a pull tab connected to a portion of the sidewall proximate to the first edge of the sidewall and the at least one separating region, wherein the pull tab is configured for grasping by a user, and when pulled, to cause the sidewall to separate in at least a portion of the at least one separating region so as to allow the user to then remove the cap from the valve region of the vascular access port to which the cap is removably attached.

2. The assembly according to claim 1, wherein the cavity is substantially cylindrical.

3. The assembly according to claim 1, wherein the at least one separating region of the cap comprises a tear strip bounded by two spaced tearable regions.

4. The assembly according to claim 1 wherein the at least one separating region of the cap comprises a tear strip bounded by a pair of spaced, substantially parallel, separating lines, the tear strip extending at least from the first edge of the sidewall toward the closed end wall of the cap and wherein the pull tab is connected to the tear strip.

5. The assembly according to claim 1 wherein the plastic comprising the cap body is comprised of a thermoplastic resin.

6. The assembly according to claim 1 wherein the cap further comprises a vent and a gas-permeable barrier to allow gas but not microorganisms to pass through the vent.

7. The assembly according to claim 1 wherein the needlefree connector is selected from the group consisting of a Y-site that comprises a needlefree connector portion that includes the vascular access port and a T-site that comprises a needlefree connector portion that includes the vascular access port.

8. The assembly according to claim 1 wherein the needlefree connector is (i) a packaged needlefree connector or (ii) a packaged vascular access connector that comprises the vascular access port wherein the vascular access connector is included in an IV set, a primary IV administration set, a secondary IV administration set, or an IV extension set.

9. A kit that comprises the assembly according to claim 8 packaged in a sealed, sterilized container.

10. A method of capping, covering, or protecting the vascular access port of the needlefree connector, comprising using the assembly according to claim 1 to protect the vascular access port to be capped, covered, or protected, thereby capping, covering, or protecting the vascular access port of the needlefree connector.

11. A method of uncapping, uncovering, or de-protecting the vascular access port of the needlefree connector included in the assembly according to claim 1, comprising using the pull tab to tear a seam in the sidewall of the cap and removing the cap to thereby uncap, uncover, or de-protect the vascular access port of the needlefree connector.

12. The assembly according to claim 1 wherein the cap further comprises a port-engaging element that is configured to engage an exterior valve surface of the vascular access port, wherein the port-engaging element is configured to provide continuing antimicrobial action when the cap is attached to a vascular access port.

13. The assembly according to claim 12 wherein the port-engaging element comprises a compressible medical grade foam.

14. The assembly according to claim 12 wherein the continuing antimicrobial action is provided by a liquid disinfectant.

15. The assembly according to claim 14 wherein the liquid disinfectant comprises 70% isopropyl alcohol.

16. A method of cleaning the vascular access port of the needlefree connector that is included in the assembly according to claim 12, the method comprising rotating the cap in relation to the vascular access port, thereby cleaning the vascular access port.

* * * * *